United States Patent [19]

Leuprecht

[11] Patent Number: 4,617,021
[45] Date of Patent: Oct. 14, 1986

[54] ABSORBENT SURGICAL DRESSING, AND PROCESS FOR MANUFACTURING SAME

[75] Inventor: Helmut Leuprecht, Vienna, Austria

[73] Assignee: Rauscher & Co. Verbandstoff- und Wattefabriken, Vienna, Austria

[21] Appl. No.: 669,477

[22] Filed: Nov. 8, 1984

[30] Foreign Application Priority Data

Nov. 9, 1983 [DE] Fed. Rep. of Germany ....... 3340530

[51] Int. Cl.⁴ ...................... A61F 13/16; A61F 13/18; A61F 13/20
[52] U.S. Cl. ...................................... 604/365; 493/340
[58] Field of Search .......................................... 604/365

[56] References Cited

U.S. PATENT DOCUMENTS 3,949,130  4/1976  Sabee et al. .......................... 604/365
3,971,379  7/1976  Chatterjee .............................. 64/365
4,102,340  7/1978  Mesek et al. ......................... 604/365
4,435,178  3/1984  Fitzgerald ............................ 604/365
4,557,777 12/1985  Sabee .................................... 604/365

Primary Examiner—Herbert S. Cockeram
Attorney, Agent, or Firm—Holman & Stern

[57] ABSTRACT

An absorbent surgical dressing comprising an envelope of hydrophobic fabric with an absorbent pad arranged within it is disclosed. The dressing of the present invention excludes the possibility of secondary lesions being caused to the wound or injury. For this purpose the internal pad forming the absorbent pad is kept loose, so as to allow slight movement of the pad in the flexible envelope tube thereby dissipating the shearing forces acting on the envelope fabric. Moreover, to obviate the secondary lesions from occurring on the wound, the loose threads at the longitudinal ends of the surgical dressing are closed by welding and severed. A process for the manufacture of the surgical dressing meeting these requirements is also disclosed.

5 Claims, 5 Drawing Figures

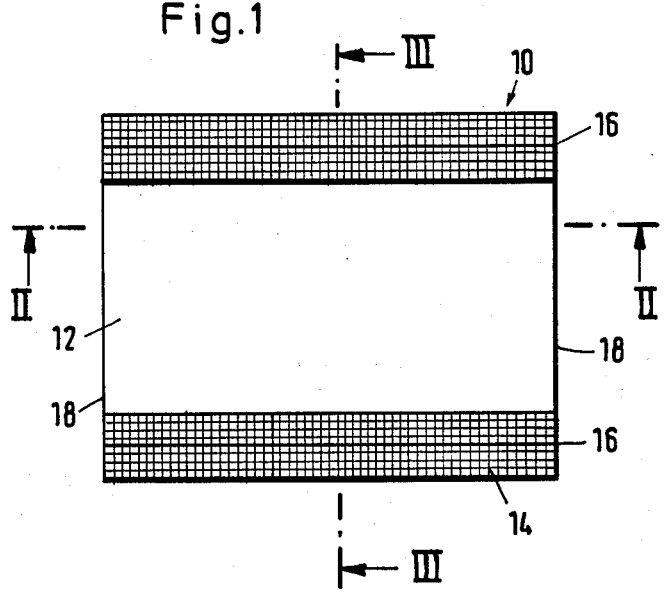
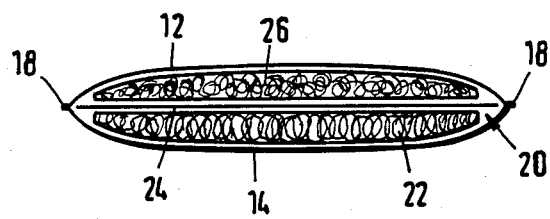
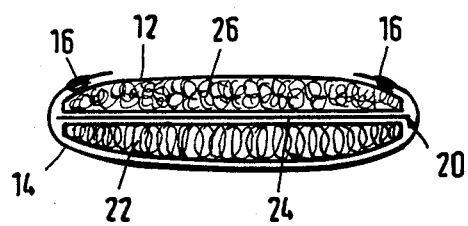

ABSORBENT SURGICAL DRESSING, AND PROCESS FOR MANUFACTURING SAME

BACKGROUND OF THE INVENTION

TECHNICAL FIELD

The present invention relates to an absorbent surgical dressing, more particularly to a dressing comprising an internally situated absorbent pad and an envelope layer which at least at the wound side has a lattice structure which does not stick to the wound. The invention also concerns a process for the manufacture of such a surgical dressing.

PRIOR ART

Absorbent surgical dressing which at the wound side have a lattice-structure envelope layer of hydrophobic material are known (German Utility Model No. 81 29 563). The use of such an envelope layer has the advantage that wound secretions can be taken up through the openings in the lattice structure by the internally situated absorbent pad, whereas, because of the material chosen (polypropylene or the like) the envelope layer does not stick to the wound. Thus secondary injuries which could be caused when changing a dressing are obviated. Healing is speeded up.

In known absorbent surgical dressings, however, the absorbent pad arranged as an internal pad in the envelope layer is connected to the envelope layer. Then if the absorbent pad is bent over on movement of the part of the body covered with the dressing, or is otherwise shifted laterally, the absorbent pad takes the envelope layer with it. This results in shearing stresses on the envelope layer and indirectly on the wound surface, and this again can cause secondary injuries.

The known absorbent surgical dressing is also cut at its longitudinal ends. This can result in the individual threads being detached from the lattice structure of the envelope layer. When a dressing is applied, the threads often stick to the wound, get covered by wound secretion, and likewise result in undesirable secondary lesions when the surgical dressing is removed.

SUMMARY OF THE INVENTION

It is, therefore, an object of the present invention to provide an absorbent dressing which does not stick to the wound.

It is another object of the present invention to provide an absorbent dressing which prevents or minimizes secondary lesions from loose threads and shearing stresses in the envelope layer affecting the wound healing.

Other objects and advantages of the present invention would become apparent as the description of the invention proceeds.

BRIEF DESCRIPTION OF THE DRAWINGS

These and other objects, features and many of the attendant advantages of the invention will be better understood upon a reading of the following detailed description when considered in connection with the accompanying drawings wherein:

FIG. 1 shows in plan view one form of embodiment of an absorbent surgical dressing according to the invention;

FIG. 2 shows a section taken on the line II—II of FIG. 1;

FIG. 3 shows a section taken on the line III—III of FIG. 1;

DETAILED DESCRIPTION OF THE INVENTION

Figure 4:
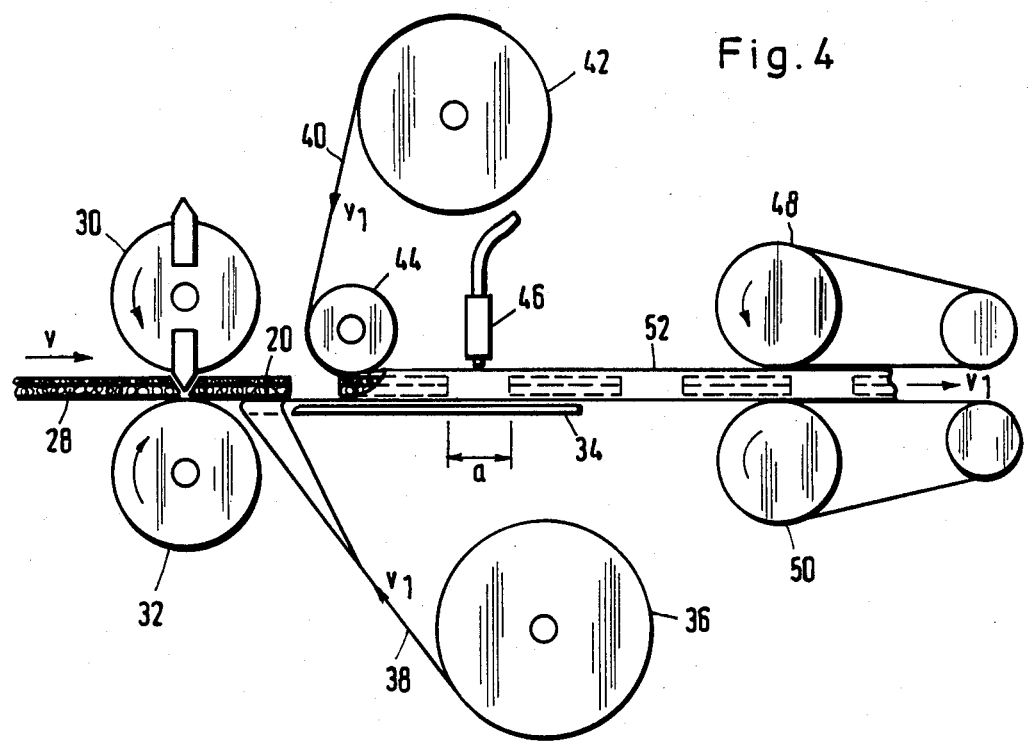
FIG. 4 shows diagrammatically an apparatus for the production of an endless flexible tube with loosely contained internal pads.

The present invention achieves the objects and advantages by providing an internal absorbent pad which is arranged loose and movable in the interior of the flexible envelope tube. When bending movements occur and when there are stresses from surface forces, the internal pad can move laterally without such movements being necessarily transmitted to the envelope layer. Thus the envelope layer remains lying securely on the wound, free of shearing forces which would cause lateral shifting. This obviates secondary lesions to the wound.

The closing of the longitudinal ends of the surgical dressing can be accomplished by any suitable means, preferably by weld seams and the severing of the surgical dressings simultaneously with the welding melts down all the loose threads. Projecting threads are cut off, and free ends are also melted down at the same time. Therefore, there can no longer be any free threads. Thus the possibility of secondary lesions which usually results from prior art dressings is also ruled out.

Of course, the provision of sufficient extra length of the flexible outer envelope tube as compared with the internal pad allows not only the formation of weld seams but also the necessary amount of play for the internal pad. Preferably, the flexible envelope tube has an extra length of at least about 10 mm. Of course, this length will be considerably greater when absorbent pads of relatively considerable thickness are employed and can be easily determined.

Although any suitable material which does not stick to the wound can be used to make the lattice structure of the envelope layer, polypropylene is preferred.

DESCRIPTION OF THE PREFERRED EMBODIMENTS

FIG. 1 shows a surgical dressing 10 in plan view of the topside, remote from the wound. The upper covering layer is made of a fleece 12 which has been given a liquid-inhibiting preparation. A polypropylene fabric 14 of a lattice structure together with said fleece 12 make up an envelope. The fabric is woven in basket weave manner, which gives a particularly soft surface. The polypropylene fabric 14 forms the entire wound-side envelope at the underside of the surgical dressing, and is folded over at the longitudinal edges in the manner illustrated on to the topside of the surgical dressing 10 and thus on the fleece 12. Here the polypropylene fabric is connected to the fleece 12 at two adhesive seams 16 which are disposed parallel to the longitudinal edges of the surgical dressing 10 somewhat inside of the top layer. To produce the adhesive seams 16 there is first applied on to the side of the fleece 12 a thread of hot-melting adhesive. The longitudinal ends of the surgical dressing 10 are closed at both sides by weld seams 18 produced by known welding techniques such as ultrasonics, thermowelding or the like. When the weld seams 18 are produced, projecting material such as loose polypropylene threads, are severed, while the free ends are welded at the same time into the weld seam. Thus, there are no longer any loose elements at the surface.

FIGS. 2 and 3 show clearly an absorbent pad 20 which is arranged as a loose pad in the interior of the envelope and construction of which has been described, supra. The absorbent pad 20 is multi-layered. This multi-layered construction, however, is shown in an exaggerated manner as regards the division into individual layers in FIGS. 2 and 3. This was simply intended to bring out the fact that the absorbent pad 20 forming the internal pad is of multi-layer type. But because of their fibrous structure, the layers constitute one coherent structure.

The absorbent pad 20 comprises at the wound side a first absorbent layer 22 of surgical cotton wool. This is followed, in the upward direction, by a multi-layer cellulose wadding mat 24. This again is followed by an absorbent layer 26 made of surgical cotton wool. Thus, because of the absorbent effect of the absorbent layers, wound secretions are taken up through the polypropylene fabric 14 into the absorbent pad 20. The hydrophobic preparation given to the fleece 12 prevents wound secretion being discharged upwards and the hydrophobic properties of the polypropylene fabric prevent discharge in the downward direction.

FIG. 4 serves to explain the process for producing an endless flexible tube with loose internal pads. From the left an endless web 28 of the multi-layer construction explained above in connection with the absorbent pad 20 is fed at a constant speed, v, to the gap between a pair of rollers comprising a cutter roller 30 and an associated roller 32, the circumferential speed of which is equal to the speed, v. Thus absorbent pads 20 are cut off by the cutter roller 30.

The individual absorbent pads 20 fall on to an endless web which travels at a higher speed $v_1$ over a platform 34 and which is made in the following way. From a drum 36 a web 38 of polypropylene fabric is drawn off at a constant speed $v_1$ and so guided over the front end of the platform 34 that the central portion of the polypropylene fabric web 38 lies flat on the topside of said platform whereas the side portions are slightly upwardly curved. The absorbent pad 20 arriving at speed v falls, after severing from the endless web 28, on the polypropylene fabric web 38 and is carried along thereby at the higher speed $v_1$. As a result there is produced between neighbouring absorbent pads 20 the spacing "a" indicated in FIG. 4.

A fleece web 40 is fed from a further drum 42 at the same speed $v_1$ as the polypropylene fabric web 38. By means of a guide roller 44 the fleece web 40 is guided with a small spacing above the surface of the absorbent pads 20, these being situated spaced from one another, and it has a thread of adhesive substance applied to it at an adhesion station 46 in the form of two nozzles (they are situated one behind the other in the Figure) stationary above the platform 34. Then a pair of rollers 48, 50 press the side edges of the polypropylene fabric web 38 on to the topside of the fleece web 40 which is provided with its thread of adhesive substance in the adhesion station 46, and thus closes the flexible envelope tube, in which the absorbent pads, arranged therein as internal pads, remain freely movable. A belt delivery 48, 50 at the same time gives the endless flexible tube the constant feed speed $v_1$. The endless flexible tube with its loose internal pads, delivered by the pair of rollers 48 and 50 is then put into interim storage. The reason for this is the fact that the next processing station (FIG. 5) operates in a timed manner and therefore requires stepwise introduction of the material to be processed. But, of course, it is also possible, by providing suitable buffer sections and with no interim storage, to combine the continuous production of the belt delivery 48, 50 with the stepwise infeed of the material at the downstream working station.

Figure 5:
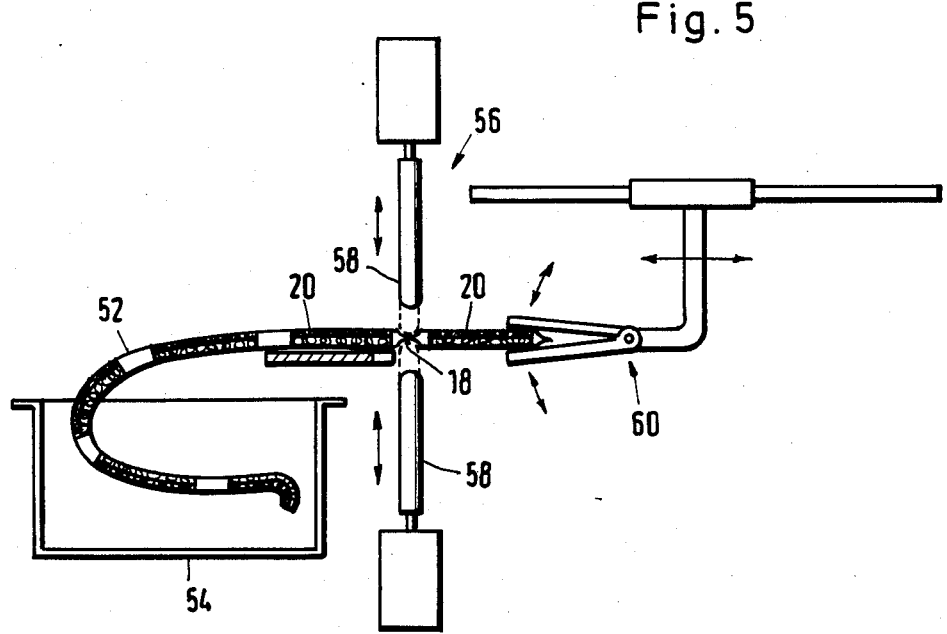
FIG. 5 shows diagrammatically an apparatus for the production of the weld seams and for severing individual surgical dressings from the endless flexible tube with its loose internal pads.

FIG. 5 shows the welding station. The endless flexible tube 52 with loose internal pads is taken from a container 54 which indicates the interim storage means. Tests in actual practice have shown that the internal pads hardly vary their positions relatively to the endless flexible envelope tube 52 through interim storage. This is possibly due to the fact that the cotton wool fibres of the absorbent layers 22 situated externally in the absorbent pad 20 catch slightly on the polypropylene fabric 14. It may also be a contributing factor that because of the compressive force in the nip gap of the belt delivery 48, 50 very small quantities of adhesive substance pass locally through the fleece 12 from the adhesive seams 16 and also form retaining points locally. These retaining points do not substantially reduce the mobility of the absorbent pads 20 relative to their envelope, but they eliminate the risk of major slipping of the internal pads out of position in the endless flexible envelope tube 52. Therefore, as far as the welding station 58 is concerned, it can be assumed that here the welding jaws 58 can always engage into the fleece space between the neighbouring absorbent pads 20 indicated by the spacing "a" in FIG. 4. The welding jaws 48 are moved to and fro by compressed-air drive means in the directions of the double arrows, and form the weld seam 18. Simultaneously with the forming of the weld seam 18, the operation of severing from the endless flexible tube is also carried out.

The severed finished surgical dressing 10 is gripped by the crocodile clip 60 and, as indicated by the double arrow, moved towards the right in FIG. 5 and deposited there in the usual way into a package or on to stock. Then the crocodile clip 60 returns and draws the endless flexible tube further to the right by the length of a finish welded surgical dressing 10, so that the next welding operation can be carried out. Of course, the endless flexible tube is held securely on the work table before the welding station 56 during the welding and severing operation by a conventional holding-down device which is not shown in FIG. 5 and is also controlled in timed manner, and is not released for forward conveyance until the crocodile clip 60 has engaged the end of the endless flexible tube.

It may be noted here that the phrase "surgical dressing" as used herein is not limited to the use of the dressing only to surgical wounds or to surgical procedures alone, but is intended to be a term of art which designates any material which is applied to cover any bodily lesion, opening or wound and the like.

It is understood that the examples and embodiments described herein are for illustrative purposes only and that various modifications or changes in light thereof will be suggested to persons skilled in the art and are to be included within the spirit and purview of this application and the scope of the appended claims.

What is claimed is:

1. An absorbent surgical dressing comprising an absorbent pad disposed internally in an envelope which at least at the wound side has a non-sticking lattice structure, the absorbent pad being capable of slight movement within the interior of said envelope.

2. The surgical dresssing of claim 1 wherein the envelope is a flexible tube having a length greater than that of the absorbent pad and is closed at both longitudinal ends by weld seams.

3. The surgical dressing of claim 2 wherein the envelope tube is at least about 10 mm greater in length than the length of the absorbent pad.

4. The surgical dressing according to claim 3, wherein the flexible envelope tube is a web of polypropylene fabric and wherein the absorbent pad comprises a fleece web wherein a first web forms the wound side and is folded at the longitudinal edges on to the side remote from the wound, and is connected in that region to a second web in two longitudinal seams which are situated parallel to the longitudinal edges.

5. The surgical dressing of claim 4 wherein the longitudinal seams are adhesive seams.

* * * * *